US011889831B2

(12) United States Patent
Schwantes

(10) Patent No.: US 11,889,831 B2
(45) Date of Patent: Feb. 6, 2024

(54) AQUEOUS MICROCAPSULE SLURRY

(71) Applicant: ENCAPSYS, LLC, Appleton, WI (US)

(72) Inventor: Todd Arlin Schwantes, Lena, WI (US)

(73) Assignees: ENCAPSYS, LLC, Appleton, WI (US); IPS STRUCTURAL ADHESIVES, INC., Compton, CA (US); IPS CORPORATION, Compton, CA (US); WATERTITE PRODUCTS, INC., Compton, CA (US); WELD-ON ADHESIVES, INC., Compton, CA (US); IPS ADHESIVES LLC, Compton, CA (US)

( * ) Notice: Subject to any disclaimer, the term of this patent is extended or adjusted under 35 U.S.C. 154(b) by 427 days.

(21) Appl. No.: 16/656,436

(22) Filed: Oct. 17, 2019

(65) Prior Publication Data

US 2020/0054006 A1    Feb. 20, 2020

Related U.S. Application Data

(62) Division of application No. 15/255,986, filed on Sep. 2, 2016, now abandoned.

(60) Provisional application No. 62/214,495, filed on Sep. 4, 2015.

(51) Int. Cl.
| | |
|---|---|
| *A01N 25/10* | (2006.01) |
| *A01N 25/04* | (2006.01) |
| *A01N 25/28* | (2006.01) |
| *A61K 8/11* | (2006.01) |
| *A61K 8/04* | (2006.01) |
| *A61K 8/81* | (2006.01) |
| *A61Q 19/00* | (2006.01) |

(52) U.S. Cl.
CPC ............ *A01N 25/10* (2013.01); *A01N 25/04* (2013.01); *A01N 25/28* (2013.01); *A61K 8/044* (2013.01); *A61K 8/11* (2013.01); *A61K 8/8147* (2013.01); *A61Q 19/00* (2013.01)

(58) Field of Classification Search
CPC ........ A01N 25/10; A01N 25/04; A01N 25/28; A61K 8/11
See application file for complete search history.

(56) References Cited

U.S. PATENT DOCUMENTS

| | | | | | |
|---|---|---|---|---|---|
| 5,073,296 | A | ‡ | 12/1991 | Kopolow | ................ A61K 8/11 424/40 |
| 5,711,951 | A | ‡ | 1/1998 | Kopolow | ............... A61K 8/062 424/40 |
| 7,772,420 | B2 | * | 8/2010 | Hermeling | ......... C08G 65/3322 524/916 |
| 7,915,215 | B2 | ‡ | 3/2011 | Bobnock | ............... A61Q 13/00 510/41 |
| 2004/0043078 | A1 | * | 3/2004 | Herault | .................. B01J 13/16 424/490 |
| 2006/0263519 | A1 | * | 11/2006 | Schwantes | ............... B01J 13/16 427/213.3 |
| 2009/0274905 | A1 | ‡ | 11/2009 | Schwantes | ............... A61K 8/11 428/40 |
| 2010/0323892 | A1 | * | 12/2010 | Levy | ....................... B01J 13/14 424/408 |
| 2014/0044761 | A1 | * | 2/2014 | Lei | ........................ A61Q 13/00 424/401 |

FOREIGN PATENT DOCUMENTS

WO    WO 2005/105291 A1  ‡  11/2005

OTHER PUBLICATIONS

Luz Sanchez-Silva, John Tsavalas, Donald Sundberg, P. Sanchez and Juan F. Rodriguez, "Synthesis and Characterization of Paraffin Wax Microcapsules with Acrylic-Based Polymer Shells", Industrial & Engineering Chemistry Research, 2010, 49, 12204-12211. (Year: 2010).*

Florentina M. Pavel, "Microemulsion Polymerization", Journal of Dispersion Science and Technology, vol. 25, No. 1, pp. 1-16, 2004. (Year: 2004).*

\* cited by examiner
‡ imported from a related application

*Primary Examiner* — Mina Haghighatian
*Assistant Examiner* — Nathan W Schlientz
(74) *Attorney, Agent, or Firm* — MUNCY, GEISSLER, OLDS & LOWE, P.C.

(57) ABSTRACT

An aqueous slurry composition containing microcapsules dispersed in an aqueous medium. The microcapsules contain an ionic acrylate copolymer shell encapsulating an oily medium. Upon drying, the microcapsules release the oily medium. The slurry is useful in delivering a variety of water-insoluble substances via an aqueous medium including cosmetic or agricultural agents.

13 Claims, No Drawings

AQUEOUS MICROCAPSULE SLURRY

CROSS-REFERENCE TO RELATED APPLICATIONS

This application is a Divisional of co-pending application Ser. No. 15/255,986, filed on Sep. 2, 2016, which claims priority of U.S. Provisional Application No. 62/214,495 filed on Sep. 4, 2015 under 35 U.S.C. § 119(e), the entire contents of both of which are hereby incorporated by reference.

FIELD OF DISCLOSURE

The present invention relates to an aqueous slurry that contains oily medium-filled microcapsules dispersed in an aqueous medium. The microcapsules have an ionic acrylate copolymer that can provide for beneficial leak resistance of the oily-medium and yet can release the oily medium upon drying/removal of the aqueous medium. The aqueous slurry is useful in a broad range of applications including agriculture and cosmetics.

BACKGROUND

Microcapsules have been used in a variety of fields. Most commonly, microcapsules found commercial utility in carbonless paper and pressure-sensitive adhesives. These microcapsules need to be durable and to rupture upon sufficient pressure. Such microcapsules have been formed from a variety of polymers including a urea-formaldehyde or a urea-melamine copolymer. Such microcapsules can be formed by interfacial polymerization wherein one monomer is in the oil phase and the other is in the aqueous phase. One phase is dispersed a droplets in the other and then polymerization proceeds at the oil-water interface to form a shell wall around the droplet. But sometimes it is advantageous have a core without the need to include a monomer.

For example, U.S. Pat. No. 5,073,296 relates to in-situ polymerization wherein the monomers are contained in a continuous aqueous phase. The polymerization forms a micrapsule wall or shell around the dispersed oil microdroplets. The monomer is a water-soluble vinyl monomer, such as vinylpyrrolidone, and optionally a comonomer. The intended result is a stable homogenous dispersion of oil microdroplets in an aqueous medium. Such an aqueous medium can be used in cosmetics wherein the microdroplets rupture upon slight pressure to release the oil, such as a skin aid.

U.S. Pat. No. 5,711,951 also relates to in-situ polymerization using water-soluble monomer to encapsulate a dispersed oil phase. The stability of the dispersion is increased by the further inclusion of a thickening agent. These suspensions are also useful in cosmetic and shampoo products.

Another kind of microcapsule suspension product is disclosed in U.S. Pat. No. 7,915,215. The shell of the microcapsule is formed from polyvinyl alcohol crosslinked by boron or persulfate ions. The microcapsules contain an oil phase such as a fragrance or cleaning product. Once the water phase is removed, however, the microcapsules break down and release the oil material. One example shows that coating the aqueous suspension onto paper and allowing it to dry resulted in the paper being oil saturated after one hour. Thus, upon removal of water, the microcapsules disintegrated and released the oil core material without the need for pressure.

The crosslinked polyvinyl alcohol microcapsule suspension of the U.S. Pat. No. 7,915,215 is quite useful. It has been discovered, however, that the storage stability of the suspension could be improved. Specifically, while in the aqueous suspension, the microcapsules sometimes leak some of the oil core, which is undesirable. It would be useful to develop an alternative aqueous microcapsule suspension. It would further be advantageous to have an alternative suspension that also begins release of the oil phase from the microcapsule upon drying without the need for pressure/force to rupture the microcapsule. It would also be useful to have a suspension that resists leaking of the oil phase core material while in the aqueous suspension but can still provide automatic release of the oil upon drying.

SUMMARY OF THE INVENTION

The present invention relates to an aqueous suspension or slurry having oil-filled microcapsules therein. Accordingly, a first aspect of the invention relates to a composition, comprising an aqueous medium having dispersed therein oily medium-containing microcapsules, wherein the oily medium-containing microcapsules comprise an ionic acrylate copolymer shell encapsulating said oily medium. The ionic acrylate copolymer can contain anionic or cationic groups pendent to an acrylate monomer. The copolymer typically is formed from a mono-functional acrylate having an ionic group and a poly-functional acrylate, though other monomers can also be present.

Another aspect of the invention relates to a process of making an aqueous slurry composition, which comprises: (a) combining an oily medium, which contains an oil-soluble polymerization initiator, with an aqueous medium, which contains a water-soluble polymerization initiator, a water-soluble mono-functional acrylate monomer having an ionic group, a water-soluble multi-functional acrylate monomer, and/or water-soluble polymerizates thereof, to form an emulsion wherein the oily medium is the dispersed phase in the form of droplets and the aqueous medium is the continuous phase; and (b) subjecting the emulsion to sufficient temperature and duration to deposit and/or polymerize an ionic acrylate copolymer shell around substantially every droplet to thereby encapsulate said oily medium and form said aqueous slurry.

A further aspect of the invention relates to the use of the aqueous slurry composition to deliver the oily medium to a substrate. For instance, a process, which comprises applying the aqueous slurry to a substrate and drying the slurry to thereby release the oily medium onto the substrate. The oily medium can contain an effective agent for cosmetics, cleaners, or agriculture, but is not limited thereto. The substrate can include skin, hair, soil, or vegetation such as plants, but is not limited thereto.

DETAILED DESCRIPTION

The present invention is based on the discovery that in an aqueous slurry containing microcapsules, an ionic acrylate copolymer can form a useful microcapsule wall or shell around an oily medium. The aqueous slurry comprises an aqueous medium having dispersed therein oily medium-containing microcapsules. The dispersion need not be a homogenous suspension of the microcapsules, i.e., the microcapsules can settle in the aqueous medium, though such a uniform suspension can be advantageous in some embodiments.

The aqueous medium comprises water and optionally other water-soluble compounds to form a solution. Additional compounds can include water-soluble or water-swellable polymers, thickeners, surfactants, and/or colorants, as well as pH adjusting agents (acid or base). The polymerization initiators or their by-products from the microcapsule formation can also be present. The aqueous medium can also comprise water-miscible solvents such as alcohols, though their presence is usually limited, if present at all, to less than 10% of the aqueous medium. Generally, water is the majority component of the aqueous medium and typically comprises at least 50%, and more typically at least 75% and often at least 90% of the aqueous medium.

Dispersed within the aqueous medium are microcapsules. These microcapsules contain an oily medium. The oily medium comprises one or more oils, optionally with oil-soluble compound(s) dissolved therein. An "oil" as used herein means a substance that is substantially immiscible in water and will provide a separate phase when mixed with water. The oil and the oily medium are not particularly limited as a variety of organic or hydrophobic substances can be advantageous dispersed in an aqueous medium for convenient application or storage via the microcapsules of the present invention. The oily medium can contain hydrocarbons, halogenated hydrocarbons, silicone oil, etc., but is not limited thereto. Typically the oily medium comprises an effective agent optionally mixed with a carrier. Effective benefit agents are substances that provide a beneficial effect for an intended use or purpose. The effective agents most commonly used in the aqueous slurry of the invention are cosmetic effective agents and agricultural effective agents. Cosmetic effective benefit agents are useful for improving the look, feel, or smell of a substrate to which it is applied. Skin and hair are typical substrates, but other substrates may include wood (cabinets, flooring, etc.) tile, and leather. Examples of cosmetic effective benefit agents include a fragrance, a UV-absorber, a moisturizer, especially a skin or hair moisturizer, etc. Two or more agents can be used in the oily medium. Agricultural effective agents are useful for improving or protecting the health or growth of animals or plants. Typically the agricultural effective agents are used on plants and include such agents as a pesticide, a herbicide, and/or a plant fertilizer. The effective agent, such as a cosmetic effective agent or an agricultural effective agent, may be used per se as an oil or can be combined with an oil carrier such as an alkane, an aromatic, etc. Also, additional compounds can be present in the oily medium in dissolved or dispersed form. For example, the polymerization initiators or their by-products from the microcapsule formation can also be present.

The oily medium is contained in microcapsules that are dispersed in the aqueous medium. The microcapsules generally have a size in the range of 1 to 50 microns, and often 5 to 25 microns, but it not particularly limited. The microcapsule shell, that is the wall that surrounds the oily medium, comprises an ionic acrylate copolymer. As used herein, "an ionic acrylate copolymer" means a polymer of two or more monomers where at least one monomer is a mono-functional acrylate having an ionic group. The ionic group can be anionic such as a carboxylic acid, a sulfonic acid, etc., or cationic such as an ammonium group. Generally the ester moiety of the mono-functional acrylate contains 1 to 6 carbon atoms, more typically 1 to 4 carbon atoms. The ionic group is generally a substituent on one of the carbon atoms of the ester moiety. Thus, for example, 2-carboxyethyl acrylate is a suitable anionic mono-functional acrylate monomer and trimethylammoniumchloride ethyl methacrylate is a suitable cationic mono-functional acrylate monomer. The ionic mono-functional acrylate should be water-soluble.

In addition to the ionic mono-functional acrylate, the copolymer contains another monomer. Typically this additional monomer is multi-functional so as to allow for cross-linking and is usually an acrylate as well; i.e., a biacrylate or triacrylate monomer. The commoner is also water-soluble. Thus a water-soluble ethoxylated trimethylolpropane triacrylate is a suitable comonomer for forming an ionic acrylate copolymer of the present invention.

Additional comonomers can also be present including non-acrylate monomers. Preferably all monomers used to form the ionic acrylate copolymer are water-soluble. Additionally, in some embodiments, the monomers are partially polymerized to form a polymerizate, also known as a prepolymer, and it is preferred that such polymerizates are also water-soluble.

The weight ratio of mono-functional acrylate to multi-functional acrylate is not particularly limited, especially if the monomers and any polymerizates remain water-soluble. Typically the weight ratio of mono-functional acrylate to multi-functional acrylate is within the range of 30:70 to 70:30, respectively; more typically 35:65 to 65:35; and often 40:60 to 60:40. Higher amounts of the multi-functional acrylate tend to reduce leakage of the oily medium from the microcapsule while in the aqueous slurry. But too high a ratio may cause microcapsule shell formation to be difficult; e.g., the polymerizates may become water-insoluble. Thus, in some embodiments, the weight ratio of mono-functional to multi-functional is about 35:65 to 60:40.

The microcapsule shell generally comprises 5 to 25% and more typically 10 to 20%, by weight, of the microcapsule.

The microcapsules are intended to contain the oily medium within them while the microcapsule remains dispersed in the aqueous medium of the slurry composition. Removal of the aqueous medium, however, should trigger the breakdown of the microcapsules and release of the oily medium. The release of the oily medium while the microcapsule is still in the slurry, e.g., leaking, is typically less than 10%, more typically less than 5%, preferably less than 2%, more preferably less than 1%, and often less than 0.5% when the slurry is stored for four weeks. The removal of the aqueous medium can result in release of the oily medium over various time periods, depending on the ionic acrylate copolymer shell material, size, and amount, but often achieves release of 50%, or over 50%, of 80-100%, or even of 95-100% of the oily medium, in some embodiments within 6 hours after the aqueous medium is removed, or in other embodiments within 24 hours, or even within 48 hours after the aqueous medium is removed. The release does not require pressure to rupture the microcapsules but instead begins spontaneously during or after the removal of the aqueous medium.

The slurry composition according to the invention is conveniently made by a process that deposits the ionic acrylate copolymer only from the aqueous phase to form a shell around the dispersed oily medium. Typically the process comprises combining an oily medium, which contains an oil-soluble polymerization initiator, with an aqueous medium, which contains a water-soluble polymerization initiator, a water-soluble mono-functional acrylate monomer having an ionic group, a water-soluble multi-functional acrylate monomer, and/or water-soluble polymerizates thereof, to form an emulsion. The emulsion is an oil-in-water emulsion wherein the oily medium is the dispersed phase in the form of droplets and the aqueous medium is the continuous phase. The emulsion is subjected to sufficient temperature and duration to deposit and/or polymerize an ionic acrylate copolymer shell around substantially every droplet to thereby encapsulate the oily medium and form the aqueous slurry of the invention. During the combining and deposition/polymerization steps, the system is usually subject to mixing in order to form and maintain the emulsion state.

Prior to the combining of the oily medium with the aqueous medium, the monomers used to form the ionic acrylate copolymer can be partially polymerized in the aqueous medium. Generally at least one monomer species remains and often two or more species remain along with the newly formed polymerizates. The type of monomers, the ratios, and the amount of reaction should be controlled so that the polymerizates and any remaining monomers are water-soluble. Additional monomers of the same or different species as the mono- and multi-functional acrylate monomers can be added before, during, and/or after the polymerizates are formed.

Once the oily medium is dispersed in the aqueous medium, the polymerization and/or deposition of the ionic acrylate copolymer can begin. The conditions used to form the shell wall correspond to polymerization conditions. The phrase "polymerization and/or deposition" is used to include polymerization from only monomers as well as polymerization involving a polymerizate from a prior partial polymerization; e.g., a prepolymer may deposit onto the droplet and react with other prepolymers and/or monomers in forming the shell. The aqueous medium may contain additional monomers of the same or different species as the mono- and multi-functional acrylate monomers, which additional monomers can be added before and/or during the polymerization and deposition step. Often the aqueous medium contains a pH adjusting agent such as an inorganic acid or base. The reaction usually takes place between 50° C. to 100° C., such as around 75° C. to 95° C. The reaction is run for sufficient time that substantially all of the droplets are encapsulated. Typically the aqueous medium contains a small amount of non-encapsulated oily medium, such that the amount of free oil in the aqueous medium is less than 5%, more typically less than 1%, and usually less than 0.5%, by weight.

Suitable initiators and/or catalysts are well known in the art. Typically azo initiators are used as both water-soluble and oil-soluble forms are commercially available. Other initiator types include sodium persulfate and ammonium persulfate. The initiators are energy activated generating free radicals when subjected to heat or other energy input. In certain embodiments initiators can include peroxy initiators, azo initiators, peroxides, and compounds such as 2,2'-azobismethylbutyronitrile, dibenzoyl peroxide. More particularly, and without limitation the free radical initiator can be selected from the group of initiators comprising an azo or peroxy initiator, such as peroxide, dialkyl peroxide, alkyl peroxide, peroxyester, peroxycarbonate, peroxyketone and peroxydicarbonate, 2,2'-azobis (isobutylnitrile), 2,2'-azobis (2,4-dimethylpentanenitrile), 2,2'-azobis(2,4-dimethylvaleronitrile), 2,2'-azobis(2-methylpropanenitrile), 2,2'-azobis (methylbutyronitrile), 1,1'-azobis (cyclohexanecarbonitrile), 1,1'-azobis(cyanocyclohexane), benzoyl peroxide, decanoyl peroxide; lauroyl peroxide; benzoyl peroxide, di(n-propyl) peroxydicarbonate, di(sec-butyl) peroxydicarbonate, di(2-ethylhexyl) peroxydicarbonate, 1,1-dimethyl-3-hydroxybutyl peroxyneodecanoate, .alpha.-cumyl peroxyneoheptanoate, t-amyl peroxyneodecanoate, t-butyl peroxyneodecanoate, t-amyl peroxypivalate, t-butyl peroxypivalate, 2,5-dimethyl 2,5-di(2-ethylhexanoyl peroxy) hexane, t-amyl peroxy-2-ethyl-hexanoate, t-butyl peroxy-2-ethylhexanoate, t-butyl peroxyacetate, di-t-amyl peroxyacetate, t-butyl peroxide, di-t-amyl peroxide, 2,5-dimethyl-2, 5-di-(t-butylperoxy)hexyne-3, cumene hydroperoxide, 1,1-di-(t-butylperoxy)-3,3,5-trimethyl-cyclohexane, 1,1-di-(t-butylperoxy)-cyclohexane, 1,1-di-(t-amylperoxy)-cyclohexane, ethyl-3,3-di-(t-butylperoxy)-butyrate, t-amyl perbenzoate, t-butyl perbenzoate, ethyl 3,3-di-(t-amylperoxy)-butyrate, and the like. Blends of initiators can also be employed.

The aqueous slurry of the present invention can be used in a variety of applications. In general the process comprises applying the aqueous slurry to a substrate and drying the slurry to thereby release the oily medium onto said substrate. The substrate can be skin or hair, such as in a cosmetic for humans, soil or plants, such as for agriculture, wood, tile, or leather, but is not limited thereto. The oily medium can contain an appropriate effective benefit agent for the intended application. For example, the oily medium can contain a fragrance, such as an aromatic compound(s), and provide a somewhat sustained release of the fragrance after drying. Benefit agents can include fragrances, perfumes, silicones, waxes, flavors, vitamins, fabric softening agents, pharmaceuticals, lubricants, cleaners, and/or biocontrol agents including biocides, herbicides, insecticides, mildewcides, and the like. The objective of such treatment is generally to leave deposited on the surfaces of substrates enough benefit agent so that there is a residual benefit imparted to the substrate surface after treatment of the substrate is completed. This feature can be useful in a cosmetic as well as a cleaner. In a another embodiment, the slurry can be applied to soil and the oily medium can contain a herbicide. Upon applying the slurry of the invention, such as by spraying, onto a substrate such as plants and/or soil, the aqueous medium will dry and the microcapsules will release the benefit agent such as herbicide over a somewhat delayed and/or sustained time frame. In further embodiments the microcapsules will release upon drying, releasing the benefit agent.

Benefit agents that are herbicides can include sulfonylurea herbicides, urea herbicides, imidazolinone herbicides, diphenyl ether herbicides, hydroxybenzonitrile herbicides, 2-(4-aryloxyphenoxy)alkanoic acid herbicides and oxime herbicides; carbamate and thiocarbamate herbicides, quaternary ammonium salt herbicides, triazole herbicides; phytohormone herbicides, including aryloxyalkanoic acid herbicides, arenecarboxylic acid herbicides, pyridinecarboxylic acid herbicides, and pyridyloxyacetic acid herbicides; 2,6-dinitroaniline herbicides, amide herbicides, and anilide herbicides, isoproturon, chlortoluron, metoxuron, linuron, monolinuron, dimefuron, diuron; imidazolinone herbicides such as imazamethabenz-methyl, imazapyr, imazaquin, and imazapyr ammonium; diphenyl ether herbicides such as bifenox, acifluorfen, fluoroglycofen ethyl, fomesafen, lactofen, and oxyfluorfen; hydroxybenzonitrile herbicides such as bromoxynil and ioxynil; 2-(4-aryloxyphenoxy)alkanoic acid herbicides such as fenoxaprop ethyl, fenoxaprop-P-ethyl fluazifop-P, fluazifop-butyl, haloxyfop-methyl, haloxyfop-etotyl, isoxapyrifop, propaquizafop-ethyl, quizalofop-ethyl, quizalofop-P-ethyl, and diclofop-methyl; carbamate/thiocarbamate herbicides such as tri-allate, di-allate, barb an, dimepiperate, molinate, and thiobencarb, difenzoquat metilsulfate, triazoles such as flupoxam, amitrole; phytohormone herbicides such as the aryloxyalkanoic acid herbicides 2,4-D, 2,4 DB, MCPA, MPCB, PCPB, MCPP (known as CMPP and mecoprop), mecoprop-P, dichlorprop, dichlorprop-P, and clomeprop; arenecarboxylic herbicide such as dicamba, the pyridinecarboxylic acid herbicide picloram; pyridyloxyacetic acid herbicides fluroxypyr, triclopyr-butotyl, and triclopyrtriethylammonium; 2,6-dinitroaniline herbicides such as pendimethalin, trifluralin, fluazinam, benfluralin, butralin and fluchloralin; oxime herbicides such as tralkoxydim, sethoxydim, alloxydim and clethodim; amide herbicides such as isoxaben, tebutam, and propyzamide. Isoxaben; anilide herbicides such as diflufenican, mefenacet and monalide; phenoxyalkanoic acid herbicides such as 2,4-dichlorophenoxy acetic acid (2,4-D); 2-methyl-4-chlorophenoxy acetic acid (MCPA); and 2-(4-chloro-2-methylphenoxy) propionic acid (mecoprop); salts, esters of N-(phosphonomethyl)glycine (glyphosate); bipyridyl herbicides, e.g. salts (in particular chloride, bromide and metho-sulphate salts) of 1,1'-dimethyl-4,4'-dipyridylium ion (paraquat) and 1,1'-ethylene-2,2'-dipyridylium ion (diquat). Benefit agents can also include agrochemicals such as fungicides, e.g., dodine; and plant growth regulators such as chlormequat, ethephon and maleic hydrazide. and mixtures of one or more of any of the foregoing.

The invention will now be described with reference to the following non-limiting examples.

EXAMPLES

Microencapsulation Process

Water phase 1, containing water and water phase initiator, is placed in a jacketed steel reactor at 40° C. with mixing at 1000 rpm with a 4-tip flat mill, and a nitrogen blanket at 100 cc/min. The batch is heated from 40 to 75° C. in 45 minutes and held at 75° C. for 45 minutes. A second water phase (containing a water-soluble multifunctional acrylate, a charged mono-functional acrylate, acid or base solution for pH adjustment (optionally), and water, and pre-heated to 60° C.) is added, and the combined water phases held at 75° C. for another 60 minutes before cooling to 60° C. in 75 minutes. An oil phase solution, containing the core oil and oil phase initiators (pre-heated to 60° C.) is added and mixing rpm increased to about 3000 for milling. After 30 minutes, batch temperature is increased to 75° C. in 30 minutes, increased from 75 to 95° C. in 7 hours, and held at 95° C. for 6 hours. To maintain emulsion stability during the acrylate wall deposition and cross-linking, milling is continued throughout the curing cycle.

The water phase initiator used was Wako V-50. The oil phase iniators were both Vazo-67 and Vazo-88. An anionic wall polymer was created using SR415 (30X ethoxylated trimethylolpropane triacrylate) and CD9055 (2-carboxyethyl acrylate). In this case pH adjustment of the water phase was done with 21.5% NaOH solution. A cationic version of the polymer was also prepared, using SR415 and TMACEMA (trimethylammoniumchloride ethyl methacrylate-a quaternary ammonium methacrylate)

Anionic Capsule Results

A series of anionic wall capsule batches was prepared and evaluated. The variables evaluated in this series include wall composition (ratio of SR415/CD9055), wall level, and V-50 initiator level. Test results for batches made with different wall compositions are shown in Table 1.

TABLE 1

| Batch | Description | Size (micron) | Free Oil (%) | Dry Release (%, 6 hour) | Hexane Leakage (%) | | | |
|---|---|---|---|---|---|---|---|---|
| | | | | | (24 hour) | (1 week) | (2 week) | (4 week) |
| TAS0217151 | Anionic, 10% Wall, 50/50 SR415/CD9055 | 13.96 | 0.41 | 105.3 | 3.8 | 8.0 | 9.1 | 11.5 |
| TAS0218151 | Anionic, 10% Wall, 60/40 SR415/CD9055 | 12.48 | 0.06 | 98.4 | 2.0 | 2.9 | 3.1 | 4.2 |
| TAS0219151 | Anionic, 10% Wall 65/35 SR415/CD9055 | 11.58 | 0.23 | 102.2 | 1.4 | 1.8 | 2.1 | 3.2 |

Four-week hexane leakage of less than 10% is very good for any acrylate wall capsule, but completely unexpected for microcapsules that show full leakage shortly after drying. The results in Table 1 suggest that an anionic capsule wall with a higher level of multi-functional acrylate (SR415) is less leaky than capsules less multi-functional monomer. This is most likely based upon higher cross-link density for capsules with more multi-functional monomer. For the anionic compositions used in this work, it was not possible to use more than 65% SR415 or the resultant polymer was no longer water-soluble.

The effect of water phase initiator level on microcapsule performance is shown in Table 2. The results suggest that, removing 50% of the water phase initiator doesn't make much of a difference on capsule leakage. Six-hour dry release is almost complete for all samples.

TABLE 2

| Batch | Description | Size (micron) | Free Oil (%) | Dry Release (%, 6 hour) | Hexane Leakage (%) | | | |
|---|---|---|---|---|---|---|---|---|
| | | | | | (24 hour) | (1 week) | (2 week) | (4 week) |
| TAS0218151 | Anionic, 10% Wall, 60/40 SR415/CD9055 | 12.48 | 0.06 | 98.4 | 2.0 | 2.9 | 3.1 | 4.2 |
| TAS0224151 | 60/40, 50% V-50 Level | 13.96 | 0.12 | 99.3 | 2.2 | 3.4 | 3.8 | 5.4 |
| TAS0303151 | 60/40, 40% V-50 Level | 17.05 | 0.21 | 95.8 | 5.2 | 12.6 | 15.6 | 21.9 |

The effect of wall level (anionic wall) on capsule performance is shown in Table 3. The results show a substantial improvement in performance when wall level is increased from 5 to 10%, but a much smaller improvement with a further increase in wall level to 20%.

TABLE 3

| Batch | Description | Size (micron) | Free Oil (%) | Dry Release (%, 6 hour) | Hexane Leakage (%) | | | |
|---|---|---|---|---|---|---|---|---|
| | | | | | (24 hour) | (1 week) | (2 week) | (4 week) |
| TAS0309151 | Anionic, 5% Wall | 13.96 | 0.22 | 99.8 | 4.8 | 17.7 | 22.5 | 33.9 |
| TAS0218151 | Anionic, 10% Wall | 12.48 | 0.06 | 98.4 | 2.0 | 2.9 | 3.1 | 4.2 |
| TAS0306151 | Anionic, 20% Wall | 15.24 | 0.08 | 97.5 | 1.8 | 2.1 | 2.2 | 2.9 |

Cationic Capsule Results

The effect of cationic capsule wall composition on capsule performance is shown in Table 4. In general, the hexane leakage and free oil results for the cationic formulations are much lower than for the anionic versions. The 6 hour dry release leakage is again almost complete.

TABLE 4

| Batch | Description | Size (micron) | Free Oil (%) | Dry Release (%, 6 hour) | Hexane Leakage (%) | | | |
|---|---|---|---|---|---|---|---|---|
| | | | | | (24 hour) | (1 week) | (2 week) | (4 week) |
| TAS0319151 | Cationic, 10% Wall, 50/50 SR415/TMACEMA | 9.13 | 0.12 | 95.5 | 0.2 | 0.4 | 0.8 | 1.3 |
| TAS0312151 | Cationic, 10% Wall, 60/40 SR415/TMACEMA | 7.38 | 0.00 | 92.9 | 0.1 | 0.1 | 0.2 | 0.3 |
| TAS0316151 | Cationic, 10% Wall, 70/30 SR415/TMACEMA | 7.38 | 0.02 | 88.9 | 0.1 | 0.1 | 0.2 | 0.3 |
| TAS0317151 | Cationic, 10% Wall, 80/20 SR415/TMACEMA | 8.58 | 0.04 | 92.8 | 0.3 | 0.4 | 0.6 | 0.7 |

The effect of wall level on capsule performance for the cationic formulations is shown in Table 5.

TABLE 5

| Batch | Description | Size (micron) | Free Oil (%) | Dry Release (%, 6 hour) | Hexane Leakage (%) | | | |
|---|---|---|---|---|---|---|---|---|
| | | | | | (24 hour) | (1 week) | (2 week) | (4 week) |
| TAS0323151 | Cationic, 5% Wall | 7.29 | 0.03 | 99.3 | 0.2 | 0.4 | 0.5 | 0.7 |
| TAS0312151 | Cationic, 10% Wall | 7.38 | 0.00 | 92.9 | 0.1 | 0.1 | 0.2 | 0.3 |
| TAS0324151 | Cationic, 20% Wall | 6.85 | 0.00 | 92.8 | 0.0 | 0.0 | 0.1 | 0.2 |

Higher wall level improves leakage, but all leakage levels are very low. Since nearly the entire core was released after a short dry time of 6 hours, additional testing was done at a much shorter dry time of 1 hour. A comparison of 1 and 6 hour dry times for the wall level series is shown in Table 6.

TABLE 6

| Batch | Description | Dry Release (%, 6 hour) | Dry Release (%, 1 hour) |
|---|---|---|---|
| TAS0323151 | Cationic, 5% Wall | 99.3 | 98.1 |
| TAS0312151 | Cationic, 10% Wall | 92.9 | 86.7 |
| TAS0324151 | Cationic, 20% Wall | 92.8 | 85.9 |

The results suggest that while with 5% wall nearly total release is achieved after only 1 hour, for higher wall levels release is not quite so rapid.

Comparison of Anionic and Cationic Capsule

Anionic and Cationic batches, produced with the same wall level and the same proportion of SR415, are compared in Table 7.

TABLE 7

| Batch | Description | Size (micron) | Free Oil (%) | Dry Release (%, 6 hour) | Hexane Leakage (%) | | | |
|---|---|---|---|---|---|---|---|---|
| | | | | | (24 hour) | (1 week) | (2 week) | (4 week) |
| TAS0218151 | Anionic, 10% Wall, 60/40 SR415/CD9055 | 12.48 | 0.06 | 98.4 | 2.0 | 2.9 | 3.1 | 4.2 |
| TAS0312151 | Cationic, 10% Wall, 60/40 SR415/TMACEMA | 7.38 | 0.00 | 92.9 | 0.1 | 0.1 | 0.2 | 0.3 |

The results show that reasonable capsules can be made with either the anionic or cationic compositions. Additionally the zeta potential was measured and the wall compositions do, in fact, result in highly anionic or highly cationic microcapsules.

While the foregoing disclosure shows illustrative embodiments of the invention, it should be noted that various changes and modifications could be made herein without departing from the scope of the invention as defined by the appended claims. The functions, steps and/or actions of the method claims in accordance with the embodiments of the invention described herein need not be performed in any particular order. Furthermore, although elements of the invention may be described or claimed in the singular, the plural is contemplated unless limitation to the singular is explicitly stated.

What is claimed is:

1. An aqueous slurry composition, comprising an aqueous medium having dispersed therein oily medium-containing microcapsules, wherein the oily medium-containing microcapsules comprise an ionic acrylate copolymer shell encapsulating said oily medium, wherein said ionic acrylate copolymer is made from only water-soluble monomers, said microcapsules release the oily medium upon removal of the aqueous medium without need for pressure to rupture the microcapsules,
wherein said ionic acrylate copolymer comprises a mono-functional acrylate monomer having an ionic group and a multi-functional acrylate monomer, and
wherein the mono-functional acrylate monomer comprises an ester moiety, the ester moiety comprises 1 to 6 carbon atoms, the ionic group comprises an ionic substituent on one of the carbon atoms of the ester moiety, and the ionic group is a carboxylic, a sulfonic, or an ammonium group.

2. The composition according to claim 1, wherein the ionic acrylate copolymer is an anionic copolymer and said mono-functional acrylate monomer contains an anionic group.

3. The composition according to claim 2, wherein said anionic group is a carboxylic acid.

4. The composition according to claim 1, wherein the ionic acrylate copolymer is a cationic copolymer and said mono-functional acrylate monomer contains the cationic group.

5. The composition according to claim 4, wherein said cationic group is the ammonium group.

6. The composition according to claim 1, wherein said multifunctional acrylate is an ethoxylated trimethylolpropane triacrylate.

7. The composition according to claim 1, wherein a weight ratio of the mono-functional acrylate monomer to the multi-functional acrylate monomer is within a range of 30:70 to 70:30, respectively.

8. The composition according to claim 1, wherein said ionic acrylate copolymer shell comprises, on average, 5 to 25% by weight of the microcapsule.

9. The composition according to claim 1, wherein said oily medium comprises a pesticide, herbicide, and/or plant fertilizer.

10. The composition according to claim 1, wherein said oily medium comprises a fragrance, a UV-absorber, and/or a skin moisturizer.

11. The composition according to claim 1, wherein said microcapsules release less than 10% of said oily medium over four weeks of storage but release all of the oily medium once the aqueous medium is removed.

12. The composition according to claim 11, wherein said microcapsules release 80-100% of said oily medium within 6 hours after aqueous medium removal.

13. The composition according to claim 12, wherein said microcapsules release less than 5% of said oily medium over four weeks of storage.

* * * * *